(12) United States Patent
Takahashi

(10) Patent No.: US 12,161,354 B2
(45) Date of Patent: Dec. 10, 2024

(54) ADHERING BODY AND ADHESION DEVICE

(71) Applicant: THE SCHOOL CORPORATION KANSAI UNIVERSITY, Suita (JP)

(72) Inventor: Tomokazu Takahashi, Suita (JP)

(73) Assignee: THE SCHOOL CORPORATION KANSAI UNIVERSITY, Suita (JP)

( * ) Notice: Subject to any disclaimer, the term of this patent is extended or adjusted under 35 U.S.C. 154(b) by 931 days.

(21) Appl. No.: 17/271,438

(22) PCT Filed: Aug. 27, 2019

(86) PCT No.: PCT/JP2019/033496
§ 371 (c)(1),
(2) Date: Feb. 25, 2021

(87) PCT Pub. No.: WO2020/045421
PCT Pub. Date: Mar. 5, 2020

(65) Prior Publication Data
US 2021/0338261 A1    Nov. 4, 2021

(30) Foreign Application Priority Data

Aug. 29, 2018  (JP) ................................ 2018-160870

(51) Int. Cl.
*A61B 17/30* (2006.01)
*A61B 17/00* (2006.01)
*A61B 17/02* (2006.01)

(52) U.S. Cl.
CPC .............. *A61B 17/30* (2013.01); *A61B 17/02* (2013.01); *A61B 2017/00017* (2013.01); *A61B 2017/0243* (2013.01); *A61B 2017/308* (2013.01)

(58) Field of Classification Search
CPC ................ A61B 17/02; A61B 17/0218; A61B 2017/0212; A61B 2017/306;
(Continued)

(56) References Cited

U.S. PATENT DOCUMENTS

| 6,447,443 B1 | 9/2002 | Keogh et al. |
| 2003/0083554 A1 * | 5/2003 | Paolitto .................. A61B 17/02 |
| | | 600/205 |

(Continued)

FOREIGN PATENT DOCUMENTS

| JP | 60056889 A | * | 4/1985 | .............. B25J 15/06 |
| JP | 05146983 A | * | 6/1993 | .............. B25J 15/06 |

(Continued)

OTHER PUBLICATIONS

International Search Report and Written Opinion for Application No. PCT/JP2019/033496, dated Oct. 15, 2019, 18 pages.

*Primary Examiner* — Christine H Matthews
*Assistant Examiner* — Julie Thi Tran
(74) *Attorney, Agent, or Firm* — McCarter & English, LLP

(57) ABSTRACT

In order to easily and stably adhere an adhering body by suction to an easily deformable flexible object, the adhering body includes an elastically deformable body that moves back and forth between a closing position at which the elastically deformable body closes a communication port and an opening position at which the elastically deformable body opens the communication port, the elastically deformable body moving, in conjunction with movement of a movable contact part to a retreat position, so as to open the communication port.

8 Claims, 10 Drawing Sheets

(58) Field of Classification Search
CPC ...... A61B 2017/308; A61B 2017/0243; A61B 17/442; F16B 47/00; B25B 11/005; B25B 11/007; A61M 1/06
See application file for complete search history.

(56) References Cited

U.S. PATENT DOCUMENTS

| | | | |
|---|---|---|---|
| 2004/0143153 A1* | 7/2004 | Sharrow | A61B 17/02 600/37 |
| 2009/0030270 A1 | 1/2009 | Arai et al. | |
| 2017/0020502 A1 | 1/2017 | Tsubouchi et al. | |

FOREIGN PATENT DOCUMENTS

| | | |
|---|---|---|
| JP | 2011-238954 A | 11/2011 |
| JP | 2013-240870 A | 12/2013 |
| JP | 2014-200874 A | 10/2014 |
| JP | 2015-208801 A | 11/2015 |
| JP | 2016-217433 A | 12/2016 |
| JP | 2017-023345 A | 2/2017 |
| WO | 2006/041014 A1 | 4/2006 |

\* cited by examiner

I-I line cross-sectional view

ADHERING BODY AND ADHESION DEVICE

TECHNICAL FIELD

The present invention relates to an adhering body and an adhesion device.

BACKGROUND ART

Examples of an adhesion device for adhering a target object by suction include a gripping device disclosed in, for example, Patent Literature 1. The gripping device disclosed in Patent Literature 1 includes: an adhering body for adhering a target object by suction; and an adhesion pump, connected to the adhering body, for generating an adhering force by suction of the target object through a suction flow path. The adhering body (i) has a communication hole that communicates with the suction flow path and (ii) includes a valve part for changing opening and closing of the communication hole. The valve part is made of a polymeric material having an elastic restoring force and has a protrusion urged to a protruding position at which the protrusion protrudes closer to the adhering body than a contact surface of the adhering body with the target object. A contact of the protrusion with the target object changes the protruding position to a withdrawal position at which the protrusion has withdrawn closer to the contact surface from the protruding position. The contact surface of the adhering body with the target object is provided with a through hole into which the protrusion of the valve part is to be inserted. According to the device disclosed in Patent Literature 1, the protruding position of the protrusion of the valve part is automatically changed to the withdrawal position by bringing the protrusion into contact with the target object so as to press the protrusion. Such a change causes the valve part to open the through hole. This allows the through hole that is in such an open state and the communication hole to be in communication with each other. This causes a sucking force from the adhesion pump to act on the target object through the through hole, so that the target object is held by suction.

Patent Literature 2 discloses a stabilizer as an adhesion device for use in coronary artery bypass grafting under a beating heart. In the coronary artery bypass grafting under a beating heart, since the heart is beating, the heart cannot be subjected to vascular anastomosis as it is. A stabilizer is an instrument that facilitates vascular anastomosis by restricting motion of only a part of the heart which part is to be subjected to vascular anastomosis. Such a stabilizer has a plurality of suction cups. An anastomosis site is stabilized by (i) reducing the pressure of the plurality of suction cups from inside of the suction cups so as to press the plurality of suction cups against an organ surface and (ii) partially sucking the organ surface so as to immobilize the organ surface.

CITATION LIST

Patent Literatures

[Patent Literature 1]
Japanese Patent Application Publication Tokukai No. 2013-240870
[Patent Literature 2]
Specification of U.S. Pat. No. 6,447,443

SUMMARY OF INVENTION

Technical Problem

However, in a case where an easily deformable flexible object such as (i) the heart surface as disclosed in Patent Literature 2 or (ii) the skin is an adhesion target, it is difficult for the device disclosed in Patent Literature 1 to adhere the adhering body by suction to the target object by a relatively weak force (e.g., a weak force by which the adhering body can be touched).

According to the device disclosed in Patent Literature 1, the adhering body needs to be adhered by suction to the target object by generating a repulsive force greater than an elastic restoring force of the valve part by bringing the protrusion of the valve part into contact with the target object so as to press the protrusion against the target object. The protrusion of the valve part contracts when the protrusion is brought into contact with the target object that is made of a relatively hard material. This causes the repulsive force to easily occur.

In contrast, the protrusion of the valve part is less likely to contract due to deformation in the target object when the protrusion is brought into contact with the target object that is the easily deformable flexible object. This causes the repulsive force to less easily occur. Thus, it is necessary to press the protrusion of the valve part against the target object by a relatively strong force in order to adhere the adhering body by suction to the target object.

Therefore, the device disclosed in Patent Literature 1 makes it difficult to easily and stably adhere the adhering body by suction to the easily deformable flexible object.

An object of an aspect of the present invention is to achieve an adhering body and an adhesion device each of which allows the adhering body to be easily and stably adhered by suction to an easily deformable flexible object.

Solution to Problem

In order to attain the object, an adhering body in accordance with an aspect of the present invention is an adhering body having a recess with which a target object forms an enclosed space, the adhering body including: a fixed contact part that is to be in contact with the target object; a communication part that is connected to a suction pump and communicates with the recess via a communication port; a movable contact part that moves, in accordance with whether the movable contact part is in contact with the target object, between (a) a protruding position at which the movable contact part protrudes closer to the target object than the fixed contact part and (b) a retreat position at which the movable contact part has retreated closer to the fixed contact part from the protruding position; and a valve body that moves back and forth between a closing position at which the valve body closes the communication port and an opening position at which the valve body opens the communication port, the valve body moving, in conjunction with movement of the movable contact part to the retreat position, so as to open the communication port.

In order to attain the object, an adhesion device in accordance with an aspect of the present invention includes: a suction pump for generating an adhering force by sucking the target object; and at least one adhering body recited above and connected to the suction pump.

Advantageous Effects of Invention

An aspect of the present invention makes it possible to easily and stably adhere an adhering body by suction to an easily deformable flexible object.

Figure 5:
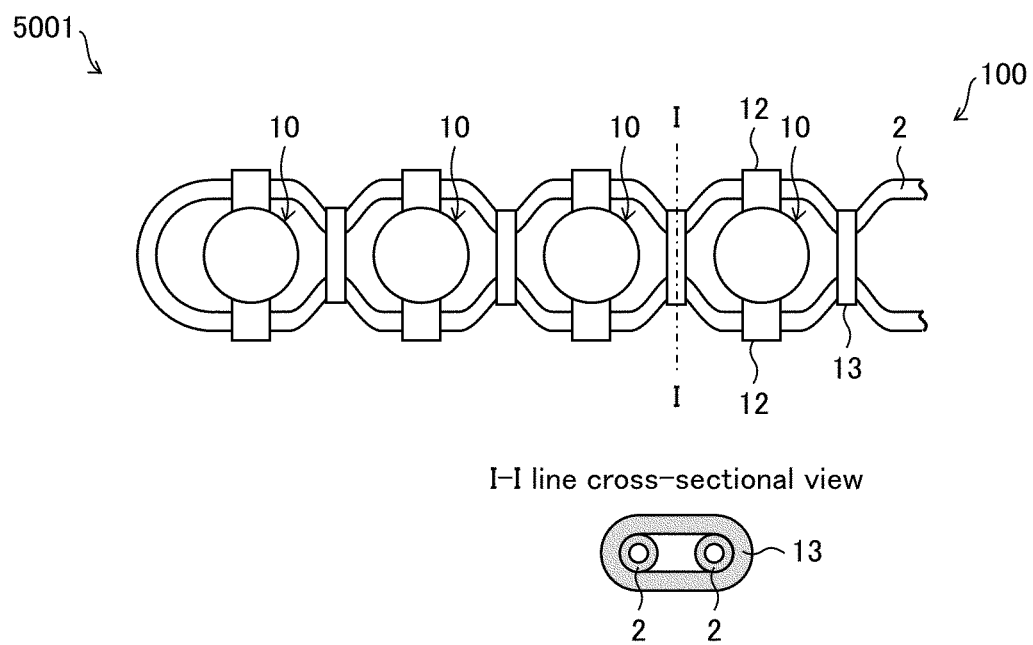
Figure 5:
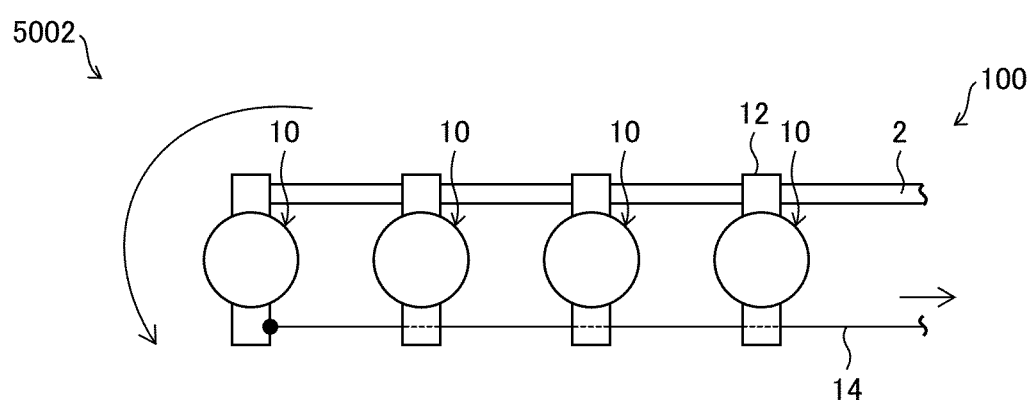

5001 of FIG. 5 is a plan view schematically illustrating a configuration of an adhesion device including a plurality of adhering bodies. 5002 of FIG. 5 is a plan view illustrating a variation of the configuration illustrated in 5001.

Figure 6:
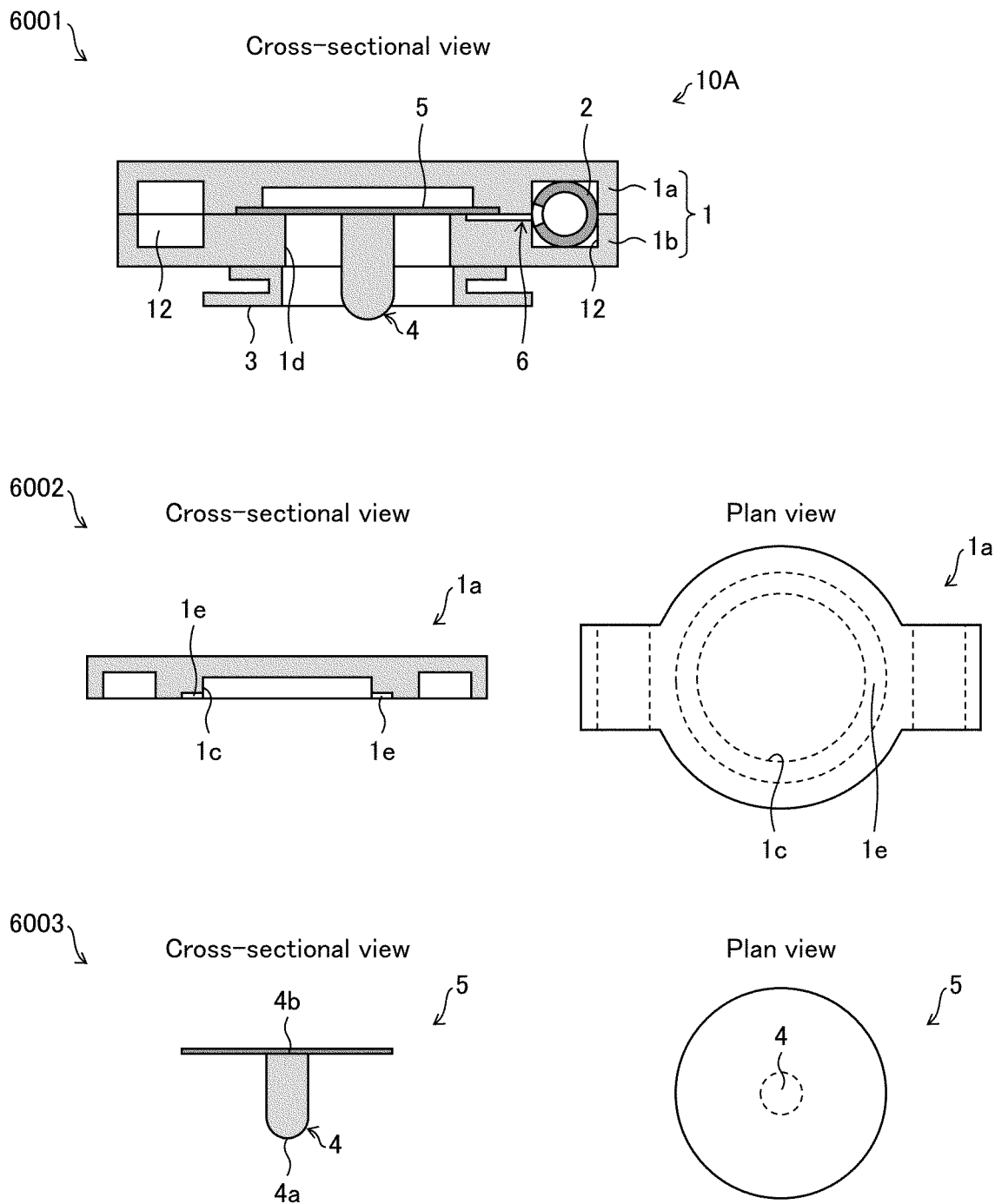

FIG. 6 schematically illustrates a configuration of an adhering body in accordance with Embodiment 2 of the present invention. 6001 is a cross-sectional view. 6002 is a cross-sectional view and a plan view each illustrating a configuration of an upper body part. 6003 is a cross-sectional view and a plan view each illustrating respective configurations of a movable contact part and an elastically deformable body.

Figure 7:
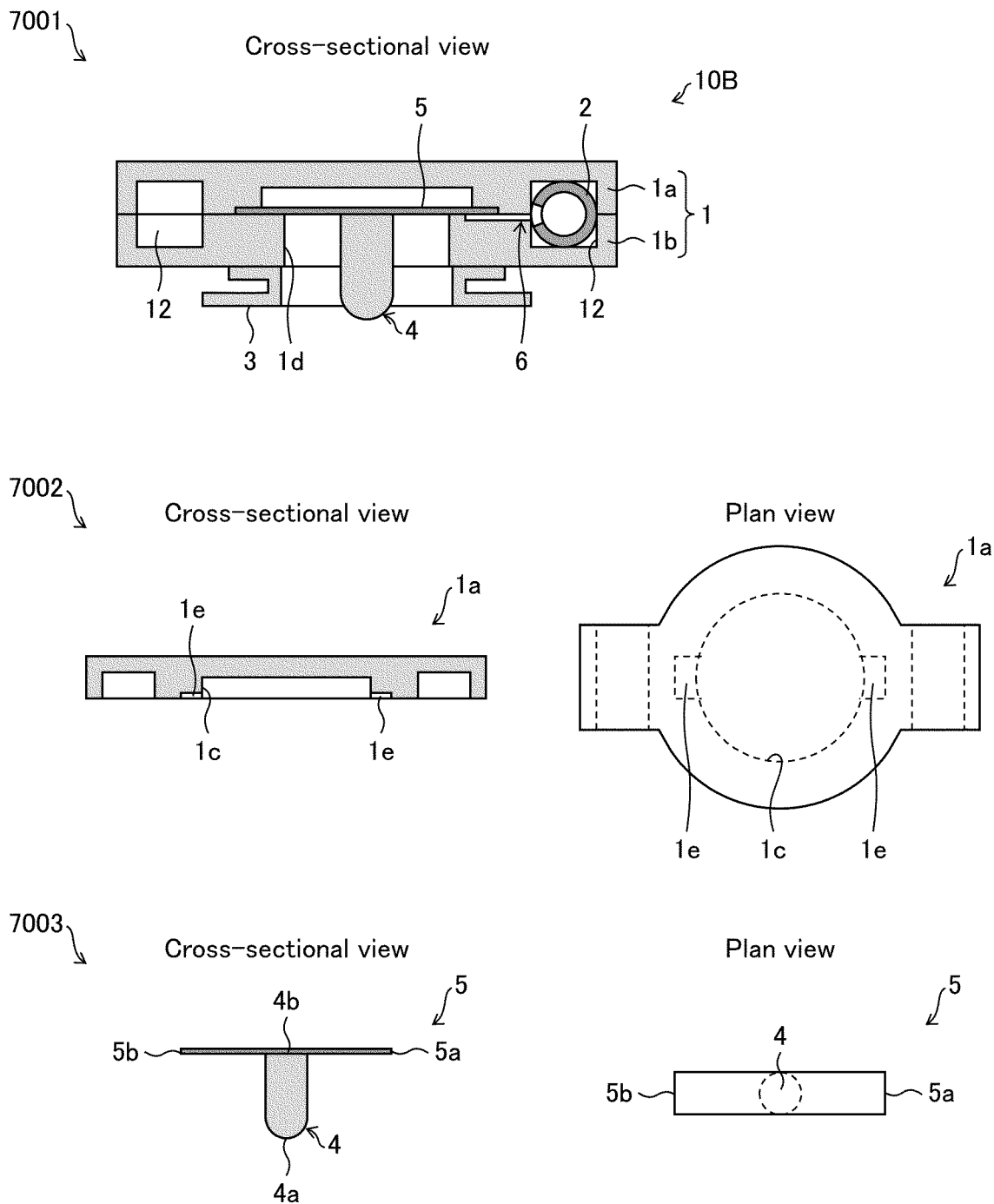

FIG. 7 schematically illustrates a configuration of an adhering body in accordance with Embodiment 3 of the present invention. 7001 is a cross-sectional view. 7002 is a cross-sectional view and a plan view each illustrating a configuration of an upper body part. 7003 is a cross-sectional view and a plan view each illustrating respective configurations of a movable contact part and an elastically deformable body.

Figure 8:
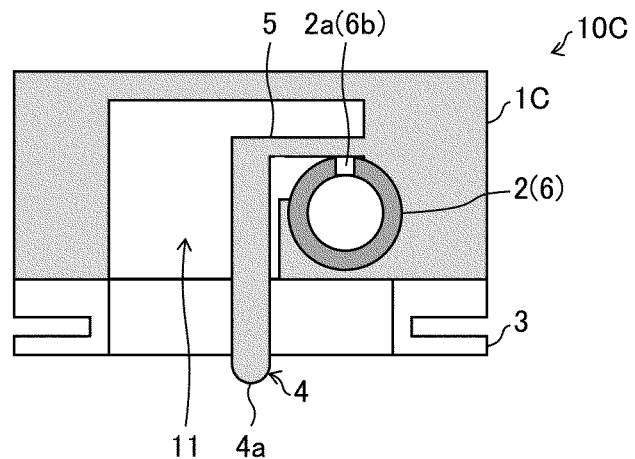

FIG. 8 is a cross-sectional view schematically illustrating a configuration of an adhering body in accordance with Embodiment 4 of the present invention.

Figure 9:
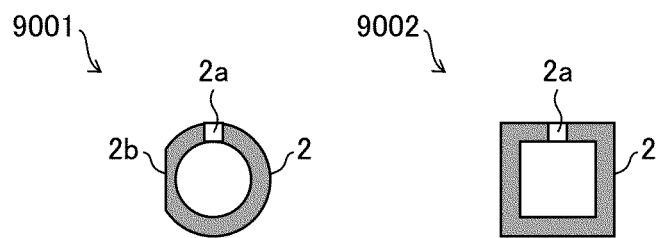

9001 and 9002 of FIG. 9 are cross-sectional views each illustrating an example of a preferable configuration of a suction tube provided in the adhering body in accordance with Embodiment 4 of the present invention.

Figure 10:
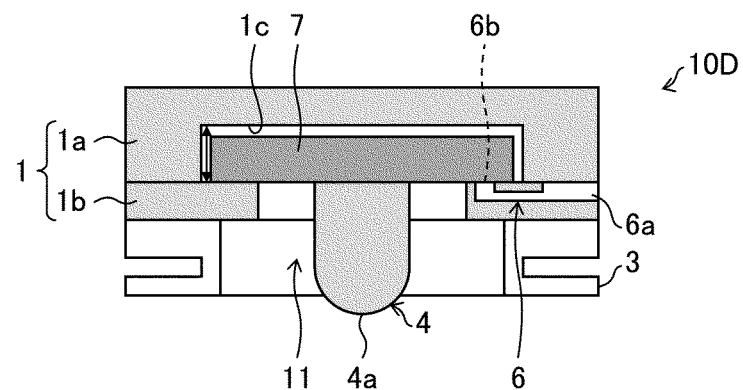

FIG. 10 is a cross-sectional view schematically illustrating a configuration of an adhering body in accordance with Embodiment 5 of the present invention.

Figure 11:
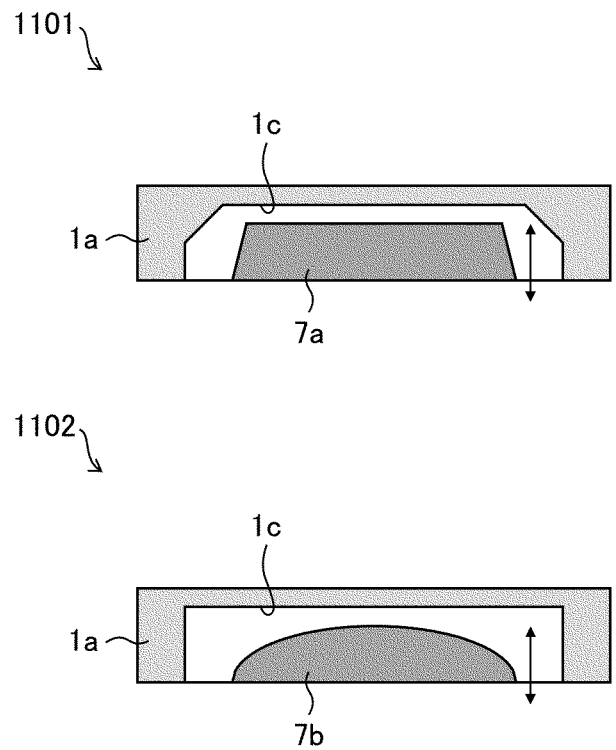

1101 and 1102 of FIG. 11 are cross-sectional views each illustrating an example of the shape of a moving valve body provided in the adhering body in accordance with Embodiment 5 of the present invention.

Figure 12:
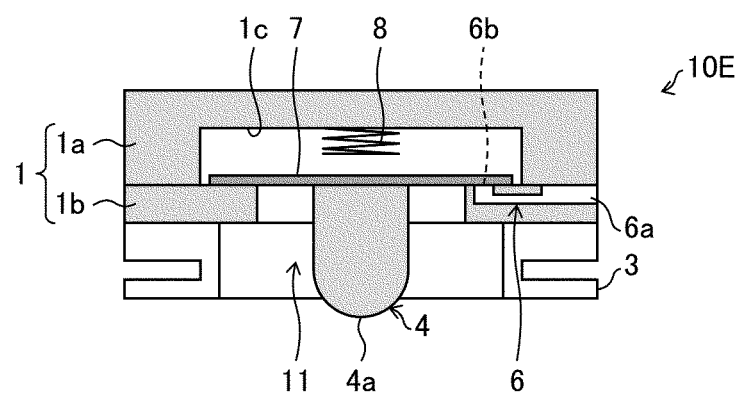

FIG. 12 is a cross-sectional view illustrating a variation of the adhering body in accordance with Embodiment 5 of the present invention.

Figure 13:
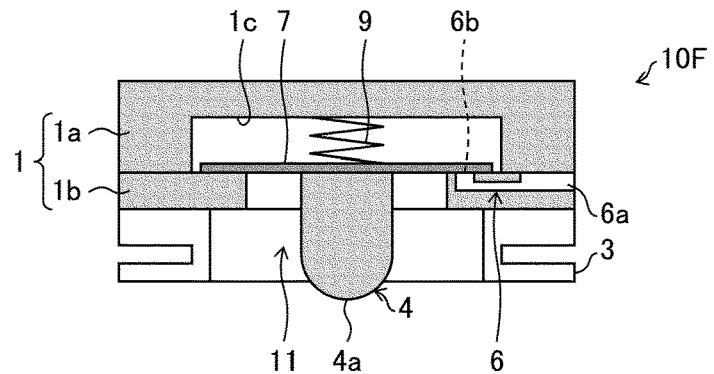

FIG. 13 is a cross-sectional view schematically illustrating a configuration of an adhering body in accordance with Embodiment 6 of the present invention.

Figure 14:
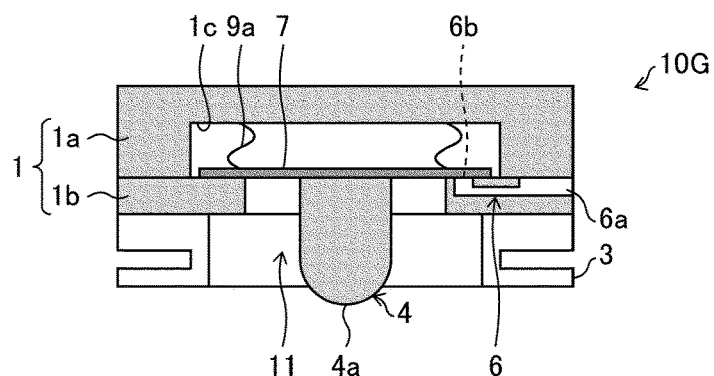

FIG. 14 is a cross-sectional view illustrating Variation 1 of the adhering body in accordance with Embodiment 6 of the present invention.

Figure 15:
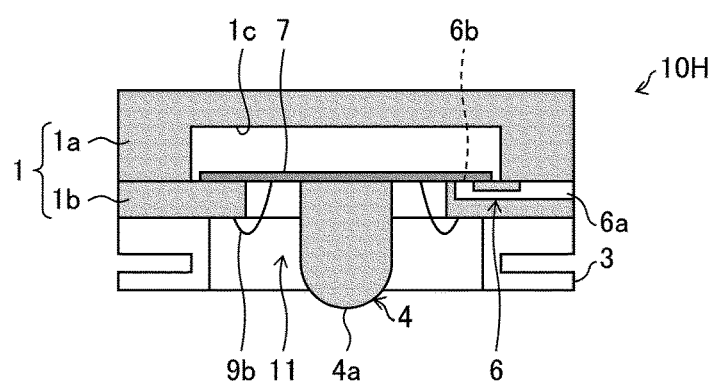

FIG. 15 is a cross-sectional view illustrating Variation 2 of the adhering body in accordance with Embodiment 6 of the present invention.

Figure 16:
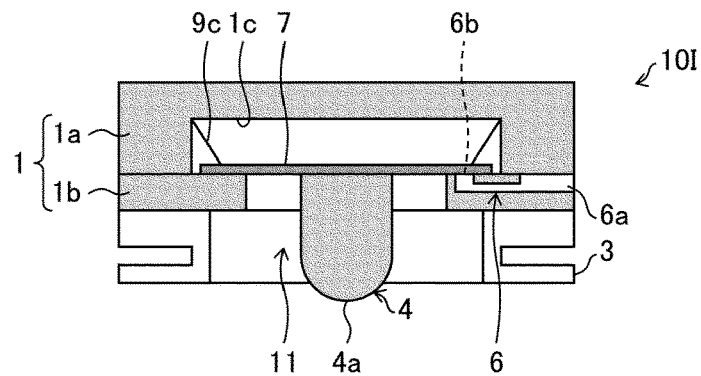

FIG. 16 is a cross-sectional view illustrating Variation 3 of the adhering body in accordance with Embodiment 6 of the present invention.

Figure 17:
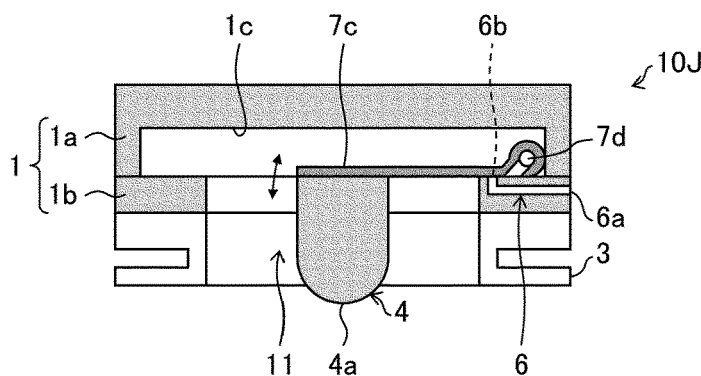

FIG. 17 is a cross-sectional view schematically illustrating a configuration of an adhering body in accordance with Embodiment 7 of the present invention, and illustrates a state in which the adhering body has not adhered a target object by suction.

Figure 18:
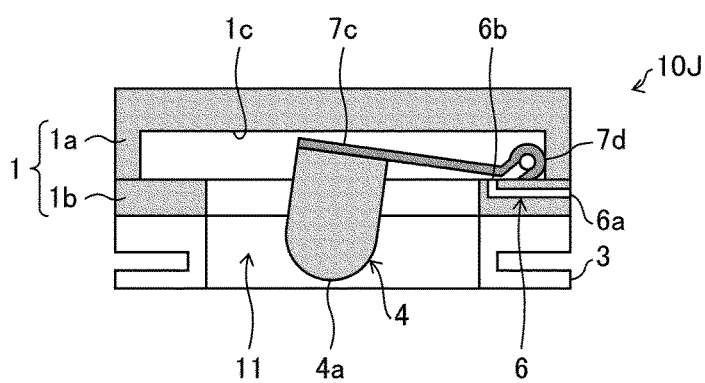

FIG. 18 is a cross-sectional view schematically illustrating the configuration of the adhering body in accordance with Embodiment 7 of the present invention, and illustrates a state in which the adhering body holds the target object by suction.

DESCRIPTION OF EMBODIMENTS

Embodiment 1

Figure 1:
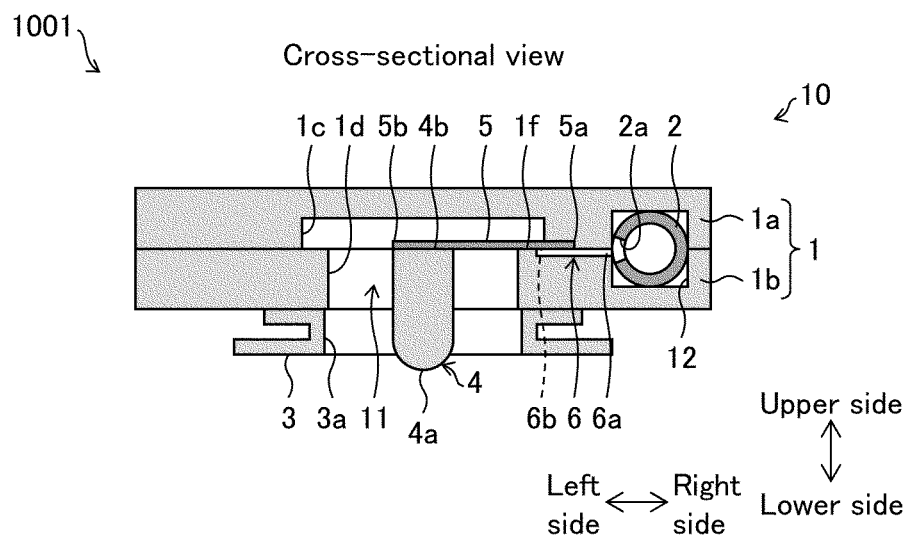
FIG. 1 schematically illustrates an adhering body in accordance with Embodiment 1 of the present invention. 1001 is a cross-sectional view, and 1002 a plan view.
Figure 1:
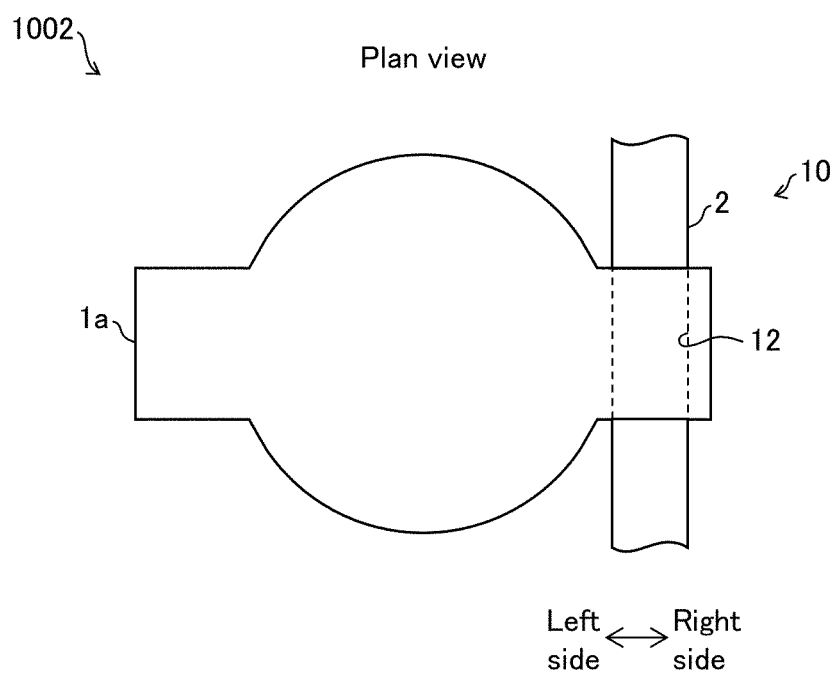

The following description will specifically discuss an embodiment of the present invention. FIG. 1 schematically illustrates an adhering body 10 in accordance with Embodiment 1. 1001 of FIG. 1 is a cross-sectional view, and 1002 of FIG. 1 is a plan view.

As illustrated in FIG. 1, the adhering body 10 in accordance with Embodiment 1 has a recess 11 with which a target object forms an enclosed space. The adhering body 10 is further provided with a tube insertion part 12 into which a suction tube 2 can be inserted.

The adhering body 10 includes a body 1, the suction tube 2, a fixed contact part 3 that is to be in contact with the target object, a movable contact part 4, an elastically deformable body 5, and a communication part 6. The body 1 is obtained by joining (i) a lower surface of an upper body part 1a and (ii) an upper surface of a lower body part 1b. The suction tube 2 is a tube for connecting the adhering body 10 to a suction pump (vacuum pump).

Assume here that, in Embodiment 1, the elastically deformable body 5 side relative to the movable contact part 4 is an upper side, and an opposite side from the elastically deformable body 5 relative to the movable contact part 4 is a lower side. Note that the lower side can also be said to be the target object side relative to the adhering body 10. Assume also that the movable contact part 4 side relative to the elastically deformable body 5 is a left side, and an opposite side from the movable contact part 4 relative to the elastically deformable body 5 is a right side.

The movable contact part 4 has a columnar shape having a tip 4a and a base end 4b. The movable contact part 4 is provided in the recess 11. As described later, the movable contact part 4 moves, in accordance with whether the movable contact part 4 is in contact with the target object, between (a) a protruding position A (see FIG. 4) at which the movable contact part 4 protrudes closer to the target object (lower side) than the fixed contact part 3 and (b) a retreat position B (see FIG. 4) at which the movable contact part 4 has retreated closer to the fixed contact part 3 (upper side) from the protruding position.

The communication part 6 is provided between the suction tube 2 and the recess 11, and constitutes a space 6a that communicates with the recess 11 via a communication port 6b. According to the adhering body 10 in accordance with Embodiment 1, the suction tube 2 is connected to the suction pump and communicates with the communication part 6. The space 6a of the communication part 6 communicates with the suction tube 2 via a suction hole 2a.

The elastically deformable body 5 (valve body) is thin plate-like and elastically deformed in a thickness direction thereof. The elastically deformable body 5 is provided so as to close the communication port 6b. The elastically deformable body 5 has (i) one end 5a that is attached to the body 1 and (ii) the other end 5b that fixes the base end 4b of the movable contact part 4. When the movable contact part 4 is located at the protruding position A and the suction pump is driven, the elastically deformable body 5 is adhered by suction to the communication part 6 so as to close the communication port 6b. Then, in response to movement of the movable contact part 4 from the protruding position A to the retreat position B, the elastically deformable body 5 is elastically deformed so as to open the communication port 6b.

Figure 2:
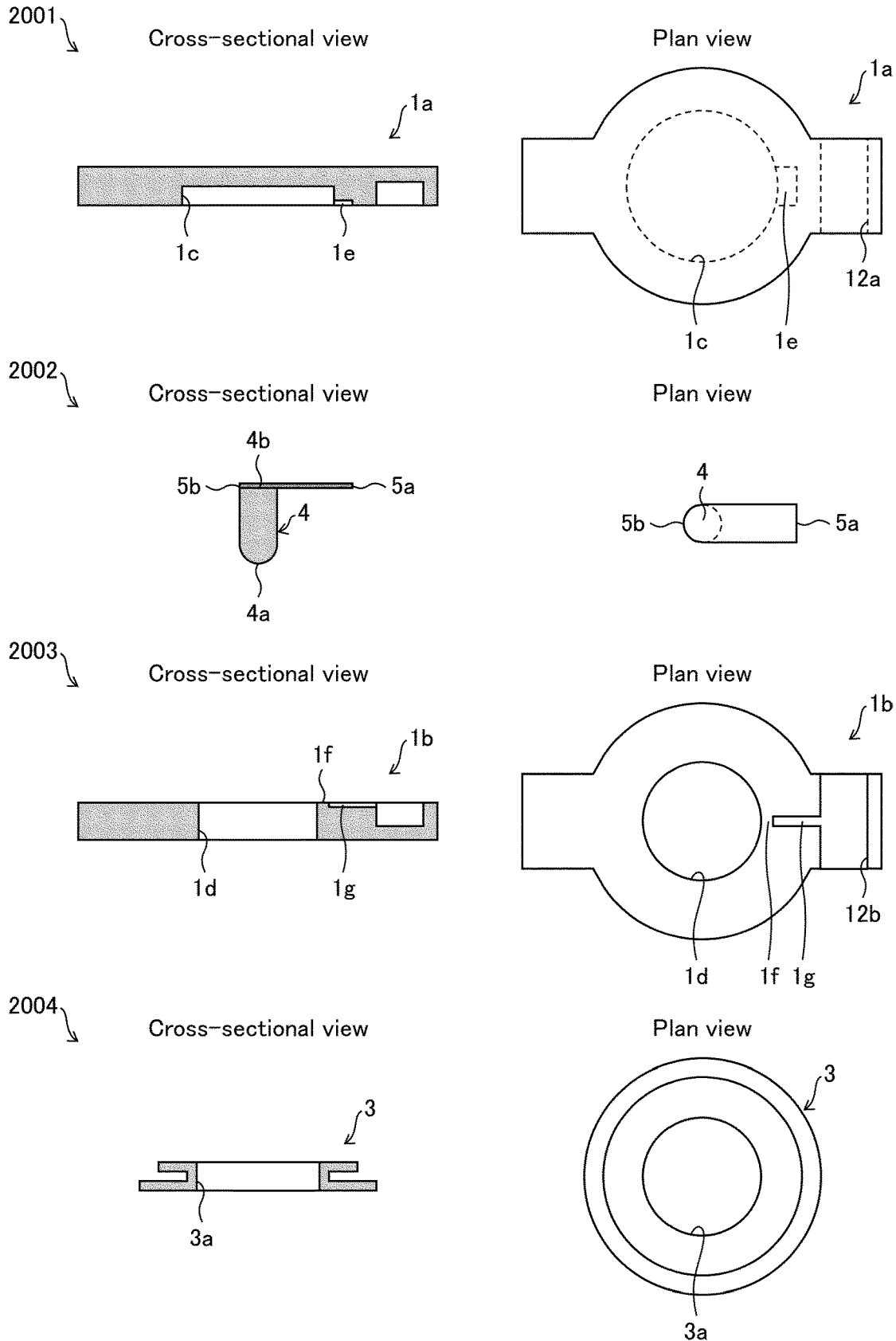
FIG. 2 schematically illustrates respective configurations of members of the adhering body illustrated in FIG. 1. 2001 is a cross-sectional view and a plan view each illustrating a configuration of an upper body part. 2002 is a cross-sectional view and a plan view each illustrating respective configurations of a movable contact part and an elastically deformable body. 2003 is a cross-sectional view and a plan view each illustrating a configuration of a lower body part. 2004 is a cross-sectional view and a plan view each illustrating a configuration of a fixed contact part.

FIG. 2 schematically illustrates respective configurations of members of the adhering body 10. 2001 of FIG. 2 is a cross-sectional view and a plan view each illustrating a configuration of the upper body part 1a. 2002 of FIG. 2 is a cross-sectional view and a plan view each illustrating respective configurations of the movable contact part 4 and the elastically deformable body 5. 2003 of FIG. 2 is a cross-sectional view and a plan view each illustrating a configuration of the lower body part 1b. 2004 of FIG. 2 is a cross-sectional view and a plan view each illustrating a configuration of the fixed contact part 3.

As illustrated in FIGS. 1 and 2001 of FIG. 2, the upper body part 1a has an appearance having a shape in which belt-shaped parts are connected to respective both right and left sides of the body, which is columnar. The body part, which has a columnar shape, has a lower surface that is provided with a cylindrical closed-end recess 1c that is recessed on the upper side. One of the belt-shaped parts that are provided on the respective both right and left sides of the body is provided with a recess 12a that constitutes the tube insertion part 12. To the right side of the recess 1c, a fitting part 1e that is fitted to an upper part of the end 5b of the elastically deformable body 5 is connected.

As illustrated in FIGS. 1 and 2002 of FIG. 2, the elastically deformable body 5 has a plate shape that is vertically elastically deformed. The elastically deformable body 5 has a cantilever structure in which the one end 5a is attached to the body 1 of the adhering body 10 and the other end 5b supports the movable contact part 4. According to Embodiment 1, the end 5b is a free end.

The end 5a of the elastically deformable body 5 supports the base end 4b of the movable contact part 4. The movable contact part 4 is provided so as to protrude from the base end 4b to the lower side. The tip 4a constitutes a curved surface so that a contact of the movable contact part 4 with the target object will have less impact on the target object. Elastic deformation of the elastically deformable body 5 causes vertical displacement of the movable contact part 4.

As illustrated in FIGS. 1 and 2003 of FIG. 2, the lower body part 1b has an appearance shape substantially identical to that of the upper body part 1a, when viewed from above. The lower body part 1b has a cylindrical hollow part 1d that vertically passes therethrough. On the upper surface of the lower body part 1b, a recess 12b that is recessed to the lower side is provided so as to correspond to the recess 12a of the upper body part 1a. To the left side of the recess 12b, a recessed groove 1g is connected. The recessed groove 1g is a groove constituting the space 6a of the communication part 6, and transversely extends toward the hollow part 1d. The recessed groove 1g is not connected to the hollow part 1d. On the upper surface of the lower body part 1b, a placement region 1f in which to place the elastically deformable body 5 is secured between the recessed groove 1g and the hollow part 1d.

As illustrated in FIGS. 1 and 2004 of FIG. 2, the fixed contact part 3 is made of a flexible material such as rubber or a synthetic resin, and has a cylindrical hollow part 3a that vertically passes through the fixed contact part 3. The hollow part 3a has a diameter identical to that of the hollow part 1d that is provided in the lower body part 1b. The fixed contact part 3, which is fixed to a surface of the body 1 which surface faces the target object, is positionally fixed relative to the body 1.

The adhering body 10 illustrated in FIG. 1 is manufactured by assembling the members illustrated in 2001 to 2004 of FIG. 2. The members are assembled by, for example, the following method. Specifically, first, the upper part of the end 5a of the elastically deformable body 5 to which the movable contact part 4 is fixed is fitted to the fitting part 1e of the upper body part 1a. Then, the lower surface of the upper body part 1a is joined to the upper surface of the lower body part 1b in the above state. Thereafter, the fixed contact part 3 is attached to the lower surface of the lower body part 1b.

As illustrated in 1001 of FIG. 1, the recess 11 of the adhering body 10 is composed of the recess 1c of the upper body part 1a, the hollow part 1d of the lower body part 1b, and the hollow part 3a of the fixed contact part 3. The space 6a of the communication part 6 is composed of the lower surface of the upper body part 1a, a part of the lower surface of the end 5a of the elastically deformable body 5, and a bottom surface and a side surface of the recessed groove 1g. The elastically deformable body 5 has (i) an upper surface that is held by the upper body part 1a of the fitting part 1e and (ii) a lower surface that is placed in the placement region 1f of the upper body part 1a.

Figure 3:
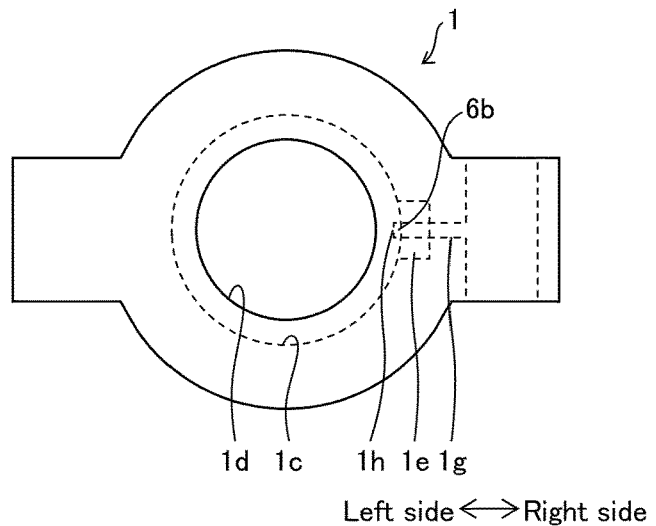
FIG. 3 is a plan view illustrating a configuration of a body manufactured by joining (i) the upper body part illustrated in 2001 of FIG. 2 and (ii) the lower body part illustrated in 2003 of FIG. 2.

FIG. 3 is a plan view illustrating a configuration of the body 1 manufactured by joining the upper body part 1a and lower body part 1b. As illustrated in FIG. 3, the recess 1c of the upper body part 1a has a diameter larger than that of the hollow part 1d of the lower body part 1b. According to the adhering body 10, the recessed groove 1g has a left side (hollow part 1d side) end 1h that is provided so as to be located on the left side with respect to a side wall of the recess 1c. In other words, the adhering body 10 is configured such that the end 1h of the recessed groove 1g is provided in the recess 1c of the upper body part 1a when viewed from above. In a case where the end 1h of the recessed groove 1g and the recess 1c of the upper body part 1a are thus provided, the communication port 6b that communicates a space inside the recess 1c (i.e., a space inside the recess 11) and a space inside the recessed groove 1g (i.e., the space 6a of the communication part 6) is formed in the body 1 obtained by joining the lower surface of the upper body part 1a and the upper surface of the lower body part 1b.

As illustrated in 1001 of FIG. 1, the elastically deformable body 5 is provided so that the lower surface of the end 5a closes the communication port 6b in the body 1. When the elastically deformable body 5 is provided so as to close the communication port 6b, the movable contact part 4 is located at the protruding position at which the tip 4a protrudes further than the fixed contact part 3. Note here that the elastically deformable body 5 is configured such that, when an upward external force is exerted on the movable contact part 4 that is provided so as to protrude closer to the target object than the fixed contact part 3, a downward elastic force is exerted on the external force.

(Configuration of Adhesion Device 100 and Adhesion Operation of Adhering Body 10)

Figure 4:
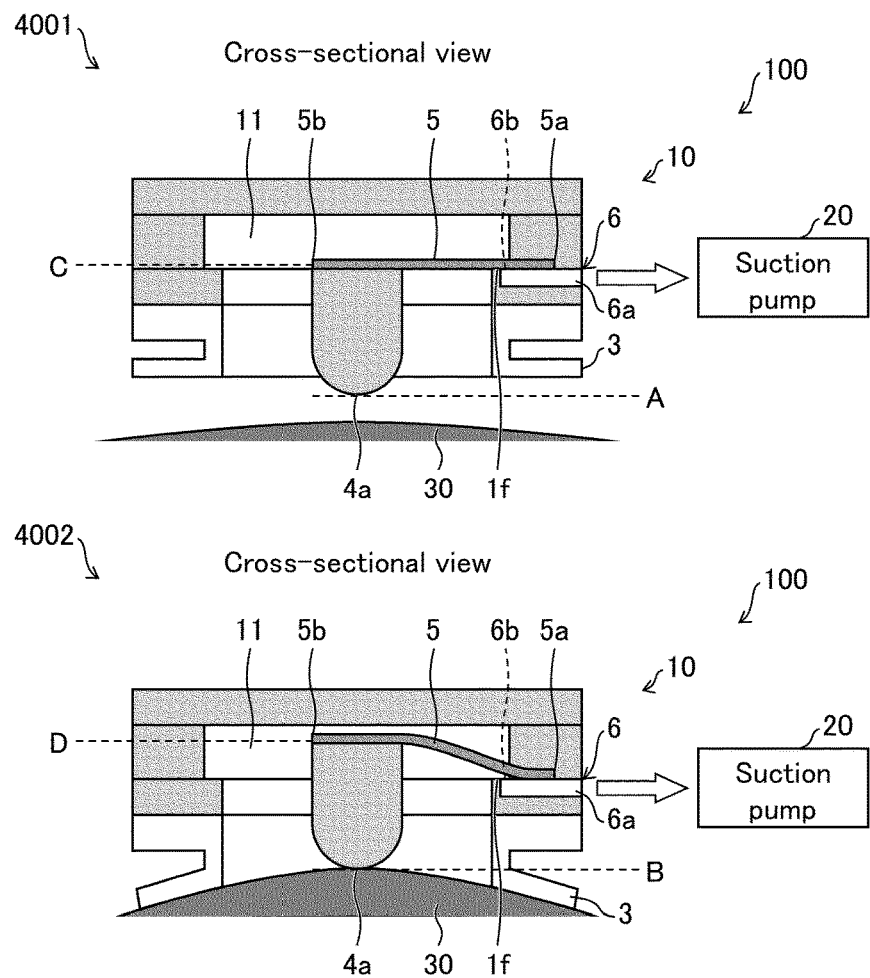
FIG. 4 is cross-sectional views (i) schematically illustrating an adhesion device including the adhering body illustrated in FIG. 1 and (ii) illustrating an adhesion operation of the adhesion device. 4001 illustrates a state in which the adhering body has not adhered the target object by suction. 4002 illustrates a state in which the adhering body holds the target object by suction.

FIG. 4 is cross-sectional views (i) schematically illustrating an adhesion device 100 in accordance with Embodiment 1 and (ii) illustrating an adhesion operation of the adhering body 10. 4001 of FIG. 4 illustrates a state in which the adhering body 10 has not adhered a target object 30 by suction. 4002 of FIG. 4 illustrates a state in which the adhering body 10 holds the target object 30 by suction.

As illustrated in 4001 and 4002 of FIG. 4, the adhesion device in accordance with Embodiment 1 includes the adhering body 10 (described earlier) and a suction pump 20. The suction pump 20 is connected to the communication part 6 of the adhering body 10 via the suction tube 2 illustrated in each of 1001 and 1002 of FIG. 1. The suction pump 20 has a function to generate an adhering force by sucking the target object 30. The following description will discuss the adhesion operation of the adhering body 10.

As illustrated in 4001 of FIG. 4, in a state in which the target object 30 is not in contact with the movable contact part 4, the movable contact part 4 is located at the protruding position A at which the tip 4a protrudes closer to the target object 30 than the fixed contact part 3. In the above state, the elastically deformable body 5 is located at a closing position C at which the elastically deformable body 5 closes the communication port 6b. At the closing position C, the elastically deformable body 5 is provided so as to close the communication port 6b. This causes the space 6a of the communication part 6 to be a closed space. Therefore, operation of the suction pump 20 in such a state results in a reduction in pressure inside the space 6a of the communication part 6.

When the movable contact part 4 is brought into contact with the target object 30 in the above state, the movable contact part 4 is automatically moved by elastic deformation of the elastically deformable body 5 to the retreat position B at which the movable contact part 4 has retreated from the protruding position A to the fixed contact part 3 side (see 4002 of FIG. 4). The elastically deformable body 5 is elastically deformed upward at this time. This causes the lower surface of the elastically deformable body 5 to be spaced from the placement region 1f. Furthermore, the communication port 6b of the communication part 6 is opened. That is, the elastically deformable body 5 is located at an opening position D at which to open the communication port 6b. As described above, in response to movement of the movable contact part 4 from the protruding position A to the retreat position B, the elastically deformable body 5 is elastically deformed so as to open the communication port 6b. Thus, such opening of the communication port 6b allows the recess 11 and the communication part 6 of the adhering body 10 to be in communication with each other. Then, operation of the suction pump 20 results in a state in which air in the recess 11 is sucked through the communication part 6. When the fixed contact part 3 of the adhering body 10 is brought into contact with the target object 30 in the above state, the pressure in a space between the recess 11 of the adhering body 10 and the target object 30 is reduced. This causes the space to be an enclosed space. Then, the adhering body 10 is held by suction on the target object 30.

In the adhesion operation of the adhering body 10, the movable contact part 4 and the elastically deformable body 5 function as valves for changing a state of communication and non-communication between the recess 11 and the adhering body 10. When the movable contact part 4 is located at the protruding position A, the recess 11 and the adhering body 10 are not in communication with each other. In contrast, when the movable contact part 4 is located at the retreat position B, the recess 11 and the adhering body are in communication with each other. Then, the elastically deformable body 5 moves back and forth between the closing position C and the opening position D in conjunction with the movable contact part 4. The elastically deformable body 5 moves in conjunction with movement of the movable contact part 4 to the retreat position B so as to open the communication port 6b. According to Embodiment 1, a contact of the movable contact part 4 with the target object 30 allows a position (state) of the movable contact part 4 to be changed from the protruding position A (a closed state) to the retreat position B (an open state). This makes it unnecessary to provide any open/close valve to the communication part 6.

For example, according to the device described in Patent Literature 1, the valve body needs to be opened by bringing the adhering body into contact with the target object by a force that is high enough to overcome the elastic restoring force of the valve body. In contrast, according to the adhesion device 100 in accordance with Embodiment 1, the communication port 6b is opened by bringing the movable contact part 4 into contact with the target object 30 by a force strong enough to elastically deform upward the elastically deformable body 5, which is thin plate-like and elastically deformed in a thickness direction thereof. This allows the adhering body 10 to be adhered by suction to the target object 30 by a relatively weak force (e.g., a weak force by which the adhering body can be touched). Thus, Embodiment 1 makes it possible to easily and stably adhere the adhering body by suction even to the target object 30 that is an easily deformable flexible object.

According to the adhesion device 100 in accordance with Embodiment 1, when the adhering body 10 is detached from the target object 30, the movable contact part 4 is automatically moved to the protruding position A by a restoring force of the elastically deformable body 5. Then, the communication port 6b of the communication part 6 is reliably closed by the elastically deformable body 5.

(Target Object 30)

The target object 30 that is suitable for the adhesion device 100 is not particularly limited provided that the target object 30 is an easily deformable flexible object. Examples of such a target object 30 include the animal skin, the human skin, an animal organ, and a human organ. Among these, the target object 30 is preferably an organ. In a case where the target object 30 is the organ, the adhesion device 100 is preferably used as a device for adhesion to the organ, the device being configured such that the adhering body 10 adheres to a surface of the organ by suction so as to immobilize a part of the surface of the organ. According to such a device for adhesion to the organ, it is particularly preferable to use the heart as the target object 30 in order to fix motion of the cardiac surface during a cardiac surgery such as coronary artery bypass grafting under a beating heart.

Examples of an article that can be used as the target object 30 include not only the animal skin, the human skin, an animal organ, and a human organ, but also a pouch container filled with, for example, liquid, powder, or sheets, and a plastic-packaged food. In a case where such an article is used as the target object 30, the adhesion device 100 is preferably used in a distribution center or the like to convey articles and/or pack the articles in boxes.

In the coronary artery bypass grafting under a beating heart, since the heart is beating, the heart cannot be subjected to vascular anastomosis as it is. This requires an instrument (stabilizer) that facilitates vascular anastomosis by restricting motion of only a partial region of the cardiac surface. Examples of such an instrument that is widely used include a suction-type instrument, disclosed in Patent Document 2, for stabilizing an anastomosis site by pressing a plurality of adhering bodies (suction cups), whose pressure has been reduced from inside of the adhering bodies, against the organ surface, and partially sucking the organ surface so as to immobilize the organ surface.

However, according to a conventional suction-type instrument, if at least one of a plurality of adhering bodies fails to suck an organ, an air leakage occurs. This causes a reduction in adhering force. This unfortunately results in difficulty in gripping of the organ due to detachment of the adhering bodies from the organ. It is also unfortunate that the necessity to press a suction cup against the organ by a great force in order to suck the organ causes great damage to the organ.

In a case where the adhesion device 100 in accordance with Embodiment 1 is used in coronary artery bypass grafting under a beating heart, no air leakage occurs, and the adhering body 10 can be pressed against the organ by a small force.

5001 of FIG. 5 is a plan view schematically illustrating a configuration of the adhesion device 100 including a plurality of adhering bodies 10. 5002 of FIG. 5 is a plan view illustrating a variation of the configuration illustrated in 5001 of FIG. 5.

According to the configuration illustrated in 5001 of FIG. 5, the plurality of adhering bodies 10 are configured to each have tube insertion parts 12 provided on respective both right and left sides thereof. The plurality of adhering bodies 10 thus configured are connected in series with respect to the suction tube 2. More specifically, the suction tube 2 is inserted in the left-side tube insertion parts 12 from an adhering body 10 disposed at one end of an array constituted by the plurality of adhering bodies 10 to an adhering body 10 disposed at the other end of the array. At the adhering body 10 disposed at the other end of the array, the suction tube 2 is bent in a U-shape so as to be inserted into the right-side tube insertion parts 12. Then, the suction tube 2 is inserted in the right-side tube insertion parts 12 from the adhering body 10 disposed at the other end of the array to the adhering body 10 disposed at the one end of the array. The tube insertion parts 12 are connected in a U-shape with respect to the array constituted by the plurality of adhering bodies 10. The adhesion device 100 illustrated in 5001 of FIG. 5 includes fastening rings 13 each for shortening the distance of the suction tube 2 between respective adjacent adhering bodies 10. The fastening rings 13 allow the array constituting the adhering bodies 10 to be easily transversely bent on the organ surface. This allows adhesion of the adhering bodies 10 in accordance with a heartbeat.

According to a conventional stabilizer, a single open/close valve is used to switch adhesion of a plurality of adhering bodies. Thus, in a case where one of the plurality of adhering bodies is detached from the organ surface due to a reduction in pressure therein, the pressure in a plurality of adhering bodies connected to that adhering body may be reduced, and all of the adhering bodies may be detached from the organ surface.

In contrast, according to the adhesion device 100 in accordance with Embodiment 1, even in a case where one of the plurality of adhering bodies 10 is detached from the target object 30, the movable contact part 4 is automatically moved to the protruding position A so as to close only the adhering body 10 thus detached. Thus, adhesion of the other adhering bodies 10 is maintained. Therefore, not all of the plurality of adhering bodies 10 will be detached from the organ surface. This allows stable adhesion performance.

The configuration illustrated in 5002 of FIG. 5 differs from the configuration illustrated in 5001 of FIG. 5 in that the plurality of adhering bodies 10 are configured to have respective tube insertion parts 12 provided on either right or left side thereof. The suction tube 2 is inserted in the tube insertion parts 12 from an adhering body 10 disposed at one end of an array constituted by the plurality of adhering bodies 10 to an adhering body 10 disposed at the other end of the array. A tensile line 14 made of metal or the like is inserted in respective ends of the plurality of adhering bodies 10 which ends are located on a side opposite from a side on which the tube insertion parts 12 are provided. Thus, for example, in a case where an operator pulls the tensile line 14 in the arrow direction, the array constituting the adhering bodies 10 is bent on the organ surface in the direction in which the tensile line 14 is pulled. Therefore, the configuration illustrated in 5002 of FIG. 5 allows adhesion of the adhering bodies 10 in accordance with a heartbeat.

Embodiment 2

The following description will specifically discuss a further embodiment of the present invention. Note that for convenience, members having functions identical to those of the respective members described in Embodiment 1 are given respective identical reference numerals, and a description of those members is omitted. FIG. 6 schematically illustrates a configuration of an adhering body 10A in accordance with Embodiment 2. 6001 of FIG. 6 is a cross-sectional view. 6002 of FIG. 6 is a cross-sectional view and a plan view each illustrating a configuration of an upper body part 1a. 6003 of FIG. 6 is a cross-sectional view and a plan view each illustrating respective configurations of a movable contact part 4 and an elastically deformable body 5.

As illustrated in 6001 to 6003 of FIG. 6, the adhering body 10A in accordance with Embodiment 2 differs from Embodiment 1 in arrangement of the elastically deformable body 5. According to Embodiment 2, the elastically deformable body 5 is a thin circular plate. The elastically deformable body 5 that is circular has an edge that is fitted to a fitting part 1e provided on a peripheral edge of a recess 1c of the upper body part 1a and is attached to a body 1. The movable contact part 4 is provided substantially at the center of the elastically deformable body 5. Even with such a configuration, it is possible to adhere the adhering body 10A by suction to a target object by a relatively weak force (e.g., a weak force by which the adhering body can be touched) by changing, for example, the thickness of the elastically deformable body 5 as appropriate. Thus, Embodiment 2 makes it possible to easily and stably adhere the adhering body 10A by suction even to the target object that is an easily deformable flexible object.

Embodiment 3

The following description will specifically discuss a still further embodiment of the present invention. Note that for convenience, members having functions identical to those of the respective members described in Embodiments 1 and 2 are given respective identical reference numerals, and a description of those members is omitted. FIG. 7 schematically illustrates a configuration of an adhering body 10B in accordance with Embodiment 3. 7001 of FIG. 7 is a cross-sectional view. 7002 of FIG. 7 is a cross-sectional view and a plan view each illustrating a configuration of an upper body part 1a. 7003 of FIG. 7 is a cross-sectional view and a plan view each illustrating respective configurations of a movable contact part 4 and an elastically deformable body 5.

As illustrated in 7001 to 7003 of Fig. 7, the adhering body 10B in accordance with Embodiment 3 differs from Embodiments 1 and 2 in arrangement of the elastically deformable body 5. According to Embodiment 3, the elastically deformable body 5 is a thin rectangular plate that is elastically deformed in a thickness direction thereof. The elastically deformable body 5 has (i) one end 5a that is attached to a body 1 so as to cover a communication port of a communication part 6 and (ii) the other end 5b that is also attached to the body 1. The movable contact part 4 is provided substantially at the center of the elastically deformable body 5. Even with such a configuration, it is possible to adhere the adhering body 10B by suction to a target object by a relatively weak force (e.g., a weak force by which the adhering body can be touched) by changing, for example, the thickness of the elastically deformable body 5 as appropriate. Thus, Embodiment 3 makes it possible to easily and stably adhere the adhering body 10B by suction even to the target object that is an easily deformable flexible object.

Embodiment 4

The following description will specifically discuss a still further embodiment of the present invention. Note that for convenience, members having functions identical to those of the respective members described in Embodiments 1 to 3 are given respective identical reference numerals, and a description of those members is omitted. FIG. 8 is a cross-sectional view schematically illustrating a configuration of an adhering body 10C in accordance with Embodiment 4.

As illustrated in FIG. 8, the adhering body 10C in accordance with Embodiment 4 differs from Embodiment 1 in that a communication part 6 is not provided in a body 1C. According to the adhering body 10C in accordance with Embodiment 4, a suction tube 2 functions as the communication part 6. Specifically, according to the adhering body 10C, the communication part 6 is the suction tube 2 connected to a suction pump, and the suction tube 2 communicates with a recess 11 via a suction hole 2a serving as a communication port.

Furthermore, according to the adhering body 10C, an elastically deformable body 5 is configured to support a movable contact part 4 by a cantilever structure. The movable contact part 4 and the elastically deformable body 5 are combined so as not to be separated from each other.

Moreover, the body 1C is combined with the movable contact part 4 and the elastically deformable body 5. When a tip 4a of the movable contact part 4 is located at a protruding position at which the tip 4a protrudes closer to a target object than a fixed contact part 3, and the suction pump is driven, the elastically deformable body 5 is adhered by suction to the suction tube 2 so as to close the suction hole 2a.

As described above, the adhering body 10C in accordance with Embodiment 4 includes (i) the fixed contact part 3 that is to be in contact with the target object, (ii) the suction tube 2 that is connected to the suction pump and communicates with the recess 11 via the suction hole 2a, and (iii) the movable contact part 4. The movable contact part 4 moves, in accordance with whether the movable contact part 4 is in contact with the target object, between (a) a protruding position at which the movable contact part 4 protrudes closer to the target object than the fixed contact part 3 and (b) a retreat position at which the movable contact part 4 has retreated closer to the fixed contact part 3 from the protruding position. Then, in response to movement of the movable contact part 4 to the retreat position, the elastically deformable body 5 is elastically deformed so as to open the suction hole 2a.

Even with such a configuration, it is possible to adhere the adhering body 10C by suction to the target object by a relatively weak force (e.g., a weak force by which the adhering body can be touched) by changing, for example, the thickness of the elastically deformable body 5 as appropriate. Thus, Embodiment 4 makes it possible to easily and stably adhere the adhering body 10C by suction even to the target object that is an easily deformable flexible object. Furthermore, according to the adhering body 10C in accordance with Embodiment 4, it is unnecessary to separately provide the communication part 6 in the body 1C. This allows the adhering body 10C to have a simple structure.

9001 and 9002 of FIG. 9 are cross-sectional views each illustrating an example of a preferable configuration of the suction tube 2 provided in the adhering body 10C in accordance with Embodiment 4. As illustrated in 9001 of FIG. 9, according to the adhering body 10C, the suction tube 2 preferably has an outer side surface part of which is a flat surface 2b. In this case, the body 1C is provided with a flat surface that is in contact with the flat surface 2b. The suction tube 2 that is provided so that the flat surface 2b is in contact with the flat surface of the body 1C can be positioned relative to the body 1C without moving in the body 1C. This eliminates a change in position of the suction hole 2a relative to the elastically deformable body 5, so that the suction hole 2a is fixed in place relative to the elastically deformable body 5. This allows the elastically deformable body 5 to stably close or open the suction hole 2a during adhesion operation of the adhering body 10C. In a preferable configuration of the suction tube 2, the suction tube 2 is not particularly limited provided that part of the outer side surface of the suction tube 2 is the flat surface 2b. For example, the suction tube 2 can be a quadrangular cylinder as illustrated in 9002 of FIG. 9.

Embodiment 5

The following description will specifically discuss a still further embodiment of the present invention. Note that for convenience, members having functions identical to those of the respective members described in Embodiments 1 to 4 are given respective identical reference numerals, and a description of those members is omitted. FIG. 10 is a cross-sectional view schematically illustrating a configuration of an adhering body 10D in accordance with Embodiment 5.

As illustrated in FIG. 10, the adhering body 10D in accordance with Embodiment 5 differs from Embodiment 1 in that the adhering body 10D includes no elastically deformable body 5 that serves as a valve body. According to the adhering body 10 in accordance with Embodiment 1, the one end 5a of the elastically deformable body 5 is fixed to the body 1 (see FIG. 1). The communication port 6b of the communication part 6 is opened and closed in a case where the elastically deformable body 5 is elastically deformed in conjunction with movement of the movable contact part 4.

However, the valve body is not limited to the elastically deformable body 5 that is elastically deformed in conjunction with movement of the movable contact part 4, but may be any member that moves back and forth, in conjunction with movement of the movable contact part 4, between a closing position at which the member closes the communication port 6b and an opening position at which the member opens the communication port 6b.

The adhering body 10D in accordance with Embodiment 5 includes a moving valve body 7. The moving valve body 7 is not fixed to a body 1. The moving valve body 7 is also provided with a movable contact part 4.

The moving valve body 7 is provided in a recess 1c of an upper body part 1a. The moving valve body 7 is placed on a lower body part 1b so as to cover a communication port 6b of a communication part 6. The moving valve body 7 is not fixed to the lower body part 1b and can be in contact with or spaced from the lower body part 1b. The moving valve body 7 vertically moves back and forth in the recess 1c. When a tip 4a of the movable contact part 4 is located at a protruding position at which the tip 4a protrudes closer to a target object than a fixed contact part 3, and a suction pump is driven, the moving valve body 7 is adhered by suction to the communication part 6 so as to close the communication port 6b.

In response to a contact of the tip 4a of the movable contact part 4 with the target object, the movable contact part 4 moves upward so as to be located at a retreat position. Then, the moving valve body 7 moves upward in conjunction with movement of the movable contact part 4 to the retreat position so as to open the communication port 6b.

Even with such a configuration, it is possible to adhere the adhering body 10D by suction to the target object by a relatively weak force (e.g., a weak force by which the adhering body can be touched) by changing, for example, the thickness of the moving valve body 7 as appropriate. Thus, Embodiment 5 makes it possible to easily and stably adhere the adhering body 10D by suction even to the target object that is an easily deformable flexible object.

1101 and 1102 of FIG. 11 are cross-sectional views each illustrating an example of the shape of the moving valve body 7. As illustrated in 1101 of FIG. 11, a moving valve body 7a preferably has a vertically extending cross section that is shaped so as to have a narrower width as the cross section extends upward. Examples of the shape of such a moving valve body 7 include a cone frustum shape, a pyramid frustum shape, and a trapezoidal frustum shape. The moving valve body 7 has dimensions that allow a clearance between the moving valve body 7 and the recess 1c to be secured while the moving valve body 7 has a bottom surface that is large enough to cover the communication port 6b. This allows the moving valve body 7 to stably vertically move back and forth in the recess 1c. Furthermore, as illustrated in 1102 of FIG. 11, a moving valve body 7b can have a protruding curved surface that bulges upward.

FIG. 12 is a cross-sectional view illustrating a variation of the adhering body in accordance with Embodiment 5. As illustrated in FIG. 12, an adhering body 10E serving as the variation differs from the adhering body 10D in that the adhering body 10E includes an elastic spring 8 provided on an upper surface of a recess 1c. When a moving valve body 7 moves upward in conjunction with movement of a movable contact part 4 to a retreat position, the elastic spring 8 is contracted by a contact with the moving valve body 7. The elastic spring 8 urges the moving valve body 7 downward. In this case, since a communication port 6b is open, the adhering body 10E is held by suction on a target object.

In response to removal of the adhering body 10E from the target object, the moving valve body 7 is moved downward by an elastic force of the elastic spring 8 so as to close the communication port 6b.

Embodiment 6

The following description will specifically discuss a still further embodiment of the present invention. Note that for convenience, members having functions identical to those of the respective members described in Embodiments 1 to 5 are given respective identical reference numerals, and a description of those members is omitted. FIG. 13 is a cross-sectional view schematically illustrating a configuration of an adhering body 10F in accordance with Embodiment 6.

As illustrated in FIG. 13, the adhering body 10F in accordance with Embodiment 6 differs from Embodiment 5 in that a moving valve body 7 is hung from an upper surface of a recess 1c via a hanging spring 9. When the moving valve body 7 is placed on a communication part 6 so as to close a communication port 6b, the hanging spring 9 exerts, on the moving valve body 7, a downward elastic force of substantially zero. The moving valve body 7, which is thus hung by the hanging spring 9, is restrained from moving in the direction perpendicular to the vertical direction. This allows the moving valve body 7 to stably vertically move back and forth in the recess 1c.

Even with such a configuration, it is possible to adhere the adhering body 10F by suction to a target object by a relatively weak force (e.g., a weak force by which the adhering body can be touched) by changing, for example, the thickness of the moving valve body 7 as appropriate. Thus, Embodiment 6 makes it possible to easily and stably adhere the adhering body 10F by suction even to the target object that is an easily deformable flexible object.

The adhering body in accordance with Embodiment 6 can be configured such that the moving valve body 7 is supported by a part of a body of the adhering body via a contraction member so that the moving valve body 7 is restrained from moving in the direction perpendicular to the vertical direction. According to the configuration illustrated in FIG. 13, the contraction member is the hanging spring 9.

FIG. 14 is a cross-sectional view illustrating Variation 1 of the adhering body in accordance with Embodiment 6. An adhering body 10G serving as Variation 1 differs from the adhering body 10F in that the contraction member is hanging wires 9a. A moving valve body 7 is hung from an upper surface of a recess 1c by two hanging wires 9a. The two hanging wires 9a are connected to respective vicinities of two opposing ends of the moving valve body 7. When the moving valve body 7 is placed on a communication part 6 so as to close a communication port 6b, the two hanging wires 9a are each connected to the moving valve body 7 while being loosened. This restrains the moving valve body 7 from moving in the direction perpendicular to the vertical direction.

FIG. 15 is a cross-sectional view illustrating Variation 2 of the adhering body in accordance with Embodiment 6. An adhering body 10H serving as Variation 2 differs from the adhering body 10F in that a moving valve body 7 is connected to a lower surface of a lower body part 1b via two wires 9b. The two wires 9b are each connected to a lower surface of the moving valve body 7. This restrains the moving valve body 7 from moving in the direction perpendicular to the vertical direction.

FIG. 16 is a cross-sectional view illustrating Variation 3 of the adhering body in accordance with Embodiment 6. An adhering body 10I serving as Variation 3 differs from the adhering body 10G in position at which two hanging wires 9c and a recess 1c are connected. One hanging wire 9c of the two hanging wires 9c is connected to a corner between an upper surface and a side surface of the recess 1c. The other the hanging wire 9c of the two hanging wires 9c is connected to a corner that is different from the corner to which the one hanging wire 9c is connected. This restrains a moving valve body 7 from moving in the direction perpendicular to the vertical direction.

Embodiment 7

The following description will specifically discuss a still further embodiment of the present invention. Note that for convenience, members having functions identical to those of the respective members described in Embodiments 1 to 6 are given respective identical reference numerals, and a description of those members is omitted. FIG. 17 is a cross-sectional view schematically illustrating a configuration of an adhering body 10J in accordance with Embodiment 7, and illustrates a state in which the adhering body 10J has not adhered a target object by suction. FIG. 18 is a cross-sectional view schematically illustrating the configuration of the adhering body 10J in accordance with Embodiment 7, and illustrates a state in which the adhering body 10J holds the target object by suction.

As illustrated in FIGS. 17 and 18, the adhering body 10J differs from Embodiment 1 in that a valve body that covers a communication port 6b has a hinge structure. More specifically, the adhering body 10J includes a rotating valve body 7c and a rotation shaft 7d each serving as the valve body. The rotation shaft 7d is attached to a body 1. The rotating valve body 7c is configured to rotate on the rotation shaft 7d. The rotating valve body 7c has an end that supports a movable contact part 4, the end being located on a side opposite from a side on which the rotation shaft 7d is provided.

As illustrated in FIG. 17, when a tip 4a of the movable contact part 4 is located at a protruding position at which the tip 4a protrudes closer to the target object than a fixed contact part 3, and a suction pump is driven, the rotating valve body 7c is adhered by suction to a communication part 6 so as to close the communication port 6b. In response to a contact of the tip 4a of the movable contact part 4 with the target object, the movable contact part 4 moves upward so as to be located at a retreat position. Then, the rotating valve body 7c rotates upward on the rotation shaft 7d in conjunction with movement of the movable contact part 4 to the retreat position (see FIG. 18). This opens the communication port 6b.

Even with such a configuration, it is possible to adhere the adhering body 10J by suction to the target object by a relatively weak force (e.g., a weak force by which the adhering body can be touched) by changing, for example, the thickness of the rotating valve body 7c as appropriate. Thus, Embodiment 7 makes it possible to easily and stably adhere the adhering body 10J by suction even to the target object that is an easily deformable flexible object.

The present invention is not limited to the embodiments, but can be altered by a skilled person in the art within the scope of the claims. The present invention also encompasses, in its technical scope, any embodiment derived by combining technical means disclosed in differing embodiments.

Aspects of the present invention can also be expressed as follows:

Adhering bodies 10 and 10A to 10J in accordance with a first aspect of the present invention are each an adhering body 10 having a recess 11 with which a target object 30 forms an enclosed space, the adhering body 10 including: a fixed contact part 3 that is to be in contact with the target object 30; a communication part 6 that is connected to a suction pump 20 and communicates with the recess 11 via a communication port 6b; a movable contact part 4 that moves, in accordance with whether the movable contact part 4 is in contact with the target object 30, between (a) a protruding position A at which the movable contact part 4 protrudes closer to the target object 30 than the fixed contact part 3 and (b) a retreat position B at which the movable contact part 4 has retreated closer to the fixed contact part 3 from the protruding position A; and a valve body (elastically deformable body 5, moving valve body 7, rotating valve body 7c) that moves back and forth between a closing position C at which the valve body closes the communication port 6b and an opening position D at which the valve body opens the communication port 6b, the valve body moving, in conjunction with movement of the movable contact part 4 to the retreat position B, so as to open the communication port 6b.

Adhering bodies 10 and 10A to 10J in accordance with a second aspect of the present invention are each configured such that, in the first aspect of the present invention, when the movable contact part 4 is located at the protruding position A and the suction pump 20 is driven, the valve body (elastically deformable body 5, moving valve body 7, rotating valve body 7c) is adhered by suction to the communication part 6 so as to close the communication port 6b.

An adhering body 10 in accordance with a third aspect of the present invention is configured such that, in the first or second aspect of the present invention, the valve body is an elastically deformable body 5 that is plate-like and elastically deformed in a thickness direction thereof, and in response to the movement of the movable contact part 4 to the retreat position B, the elastically deformable body 5 is elastically deformed so as to open the communication port 6b.

An adhering body 10 in accordance with a fourth aspect of the present invention is configured such that, in the third aspect of the present invention, the elastically deformable body 5 has a cantilever structure in which the elastically deformable body 5 has ends one (one end 5a) of which is attached to a body 1 of the adhering body 10 so as to cover the communication port 6b and the other (the other end 5b) of which supports the movable contact part 4.

An adhering body 10 in accordance with a fifth aspect of the present invention is configured, in any one of the first through fourth aspects of the present invention, to further include: a suction tube 2 that is connected to the suction pump 20 and communicates with the communication part 6.

An adhering body 10C in accordance with a sixth aspect of the present invention is configured such that, in any one of the first through fourth aspects of the present invention, the communication part 6 is a suction tube 2 that is connected to the suction pump 20, and the suction tube 2 communicates with the recess 11 via the communication port (suction hole 2a).

An adhesion device 100 in accordance with a seventh aspect of the present invention includes: a suction pump 20 for generating an adhering force by sucking the target object 30; and at least one adhering body 10 recited in any one of the first through sixth aspects of the present invention and connected to the suction pump 20.

An adhesion device 100 in accordance with an eighth aspect of the present invention is configured such that, in the seventh aspect of the present invention, the at least one adhering body 10 comprises a plurality of adhering bodies 10, the adhesion device 100 further including: a suction tube 2 that is connected to the suction pump, the plurality of adhering bodies 10 being connected in series with respect to the suction tube.

An adhesion device 100 in accordance with a ninth aspect of the present invention is configured such that, in the seventh or eighth aspect of the present invention, the target object 30 is an organ, and the adhesion device 100 is a device for adhesion to the organ, the device being configured such that the at least one adhering body 10 adheres to a surface of the organ by suction so as to immobilize a part of the surface of the organ.

The present invention is not limited to the embodiments, but can be altered by a skilled person in the art within the scope of the claims. The present invention also encompasses, in its technical scope, any embodiment derived by combining technical means disclosed in differing embodiments. Further, it is possible to form a new technical feature by combining the technical means disclosed in the respective embodiments.

REFERENCE SIGNS LIST

1 Body
2 Suction tube
3 Fixed contact part
4 Movable contact part
5 Elastically deformable body (valve body)
5a End (one end)
5b End (the other end)
6 Communication part
6b Communication port
7 Moving valve body (valve body)
7c Rotating valve body (valve body)
10 Adhering body
20 Suction pump
30 Target object
100 Adhesion device
A Protruding position
B Retreat position
C Closing position
D Opening position

The invention claimed is:

1. An adhering body having a recess with which a target object forms an enclosed space, said adhering body comprising:
   a fixed contact part that is to be in contact with the target object;
   a communication part that is configured to be connected to a suction pump and communicates with the recess via a communication port;
   a movable contact part that moves, in accordance with whether the movable contact part is in contact with the target object, between (a) a protruding position at which the movable contact part protrudes closer to the target object than the fixed contact part and (b) a retreat position at which the movable contact part has retreated closer to the fixed contact part from the protruding position; and
   a valve body that moves back and forth between a closing position at which the valve body closes the communication port and an opening position at which the valve body opens the communication port,
   the valve body moving, in conjunction with movement of the movable contact part to the retreat position, to open the communication port,
   the valve body being an elastically deformable body that is plate-like and configured to elastically deform in a thickness direction thereof, and
   the elastically deformable body being elastically deformable to open the communication port in response to the movement of the movable contact part to the retreat position.

2. The adhering body as set forth in claim 1, wherein, when the movable contact part is located at the protruding position and the suction pump is driven, the valve body is adhered by suction to the communication part so as to close the communication port.

3. The adhering body as set forth in claim 1, wherein the elastically deformable body has a cantilever structure in which the elastically deformable body has ends, one of which is attached to a body of the adhering body so as to cover the communication port and the other of which supports the movable contact part.

4. An adhering body as set forth in claim 1, further comprising:
   a suction tube that is configured to be connected to the suction pump and communicates with the communication part.

5. The adhering body as set forth in claim 1, wherein:
   the communication part is a suction tube that is configured to be connected to the suction pump, and
   the suction tube communicates with the recess via the communication port.

6. An adhesion device comprising:
   the suction pump for generating an adhering force by sucking the target object; and
   at least one adhering body recited in claim 1 and connected to the suction pump.

7. The adhesion device as set forth in claim 6, wherein the at least one adhering body comprises a plurality of adhering bodies,
   said adhesion device further comprising:
   a suction tube that is connected to the suction pump,
   the plurality of adhering bodies being connected in series with respect to the suction tube.

8. The adhesion device as set forth in claim 6, wherein:
   the target object is an organ, and
   the adhesion device is a device for adhesion to the organ, the device being configured such that the at least one adhering body adheres to a surface of the organ by suction so as to immobilize a part of the surface of the organ.

* * * * *